(12) United States Patent
Roche et al.

(10) Patent No.: US 8,098,544 B2
(45) Date of Patent: Jan. 17, 2012

(54) METHOD AND SYSTEM FOR ENHANCING ACCURACY IN ULTRASONIC ALIGNMENT

(75) Inventors: Martin Roche, Fort Lauderdale, FL (US); Jason McIntosh, Sugar Hill, GA (US); Marc Boillot, Plantation, FL (US)

(73) Assignee: Orthosensor, Inc., Sunrise, FL (US)

( * ) Notice: Subject to any disclaimer, the term of this patent is extended or adjusted under 35 U.S.C. 154(b) by 29 days.

(21) Appl. No.: 12/764,078

(22) Filed: Apr. 20, 2010

(65) Prior Publication Data
US 2010/0204575 A1  Aug. 12, 2010

Related U.S. Application Data

(63) Continuation-in-part of application No. 12/146,445, filed on Jun. 26, 2008, now Pat. No. 7,724,355, which is a continuation-in-part of application No. 11/562,410, filed on Nov. 21, 2006, now Pat. No. 7,414,705.

(60) Provisional application No. 60/740,358, filed on Nov. 29, 2005, provisional application No. 61/291,725, filed on Dec. 31, 2009.

(51) Int. Cl.
*G01S 3/80* (2006.01)
(52) U.S. Cl. ......... 367/124; 367/117; 367/118; 367/125
(58) Field of Classification Search .................. 367/117, 367/118, 124, 125
See application file for complete search history.

(56) References Cited

U.S. PATENT DOCUMENTS

| | | | |
|---|---|---|---|
| 5,570,099 A * | 10/1996 | DesJardins | .................... 342/378 |
| 6,546,277 B1 | 4/2003 | Franck et al. | |
| 7,139,418 B2 | 11/2006 | Abovitz et al. | |
| 7,309,339 B2 | 12/2007 | Cusick | |
| 7,392,076 B2 | 6/2008 | Moctezuma de La Barrera | |
| 7,395,181 B2 | 7/2008 | Foxlin | |
| 7,477,926 B2 | 1/2009 | McCombs | |
| 7,559,931 B2 | 7/2009 | Stone | |
| 7,604,645 B2 | 10/2009 | Barzell et al. | |
| 7,636,595 B2 | 12/2009 | Marquart | |
| 7,657,298 B2 | 2/2010 | Moctezuma de la Barrera et al. | |
| 7,660,623 B2 | 2/2010 | Hunter et al. | |
| 7,681,448 B1 | 3/2010 | Preston et al. | |
| 7,685,861 B2 | 3/2010 | Lynch et al. | |
| 7,689,032 B2 | 3/2010 | Strassenburg-Kleciak | |
| 2004/0024309 A1 | 2/2004 | Ferre et al. | |
| 2004/0236424 A1 | 11/2004 | Berez et al. | |
| 2004/0254584 A1 | 12/2004 | Sarin et al. | |
| 2005/0125117 A1* | 6/2005 | Breed | .............................. 701/29 |

* cited by examiner

*Primary Examiner* — Timothy A Brainard
(74) *Attorney, Agent, or Firm* — Marc Boillot

(57) ABSTRACT

A method for short range alignment using ultrasonic sensing is provided. The method includes shaping an ultrasonic pulse on a first device to produce a pulse shaped signal and transmitting the pulse shaped signal from the first device to a second device, receiving the pulse shaped signal and determining an arrival time of the pulse shaped, identifying a relative phase of the pulse shaped signal with respect to a previously received pulse shaped signal, identifying a pointing location of the first device from the arrival time and the relative phase, determining positional information of the pointing location of the first device, and reporting an alignment of three or more points in three-dimensional space. Other embodiments are disclosed.

13 Claims, 7 Drawing Sheets

US 8,098,544 B2

METHOD AND SYSTEM FOR ENHANCING ACCURACY IN ULTRASONIC ALIGNMENT

CROSS REFERENCE

This application is a Continuation-In-Part of U.S. patent application Ser. No. 12/146,445 filed on Jun. 26, 2008, that application a Continuation-In-Part of U.S. patent application Ser. No. 11/562,410 filed Nov. 21, 2006 claiming the priority benefit of U.S. Provisional Patent Application No. 60/740,358 filed Nov. 29, 2005, the entire contents of which are hereby incorporated by reference. This application also claims priority benefit to Provisional Patent Application No. 61/291,725 filed Dec. 31, 2009, the entire contents of which are hereby incorporated by reference.

FIELD

The present invention generally relates to the field of user interface navigation, and more particularly, to pointing devices.

INTRODUCTION

Motion sensing systems detect movement or general location of an object. As one example, a radar unit transmits and receives high energy signals for detecting a large metallic object. High energy signals reflect of the object due to the properties of the metal. As another example, a weather system tracks storm movement. The system determines the storm distance by measuring a time difference between when a radar signal was emitted and when a reflection of the radar signal was received. As yet another example, a security system detects a presence of an object entering in close proximity by assessing threshold measurements of transmitted and received energy signals.

Such systems provide general proximity detection and movement tracking. A need however can arise for determining accurate alignment of objects.

DETAILED DESCRIPTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

In one embodiment, a system for short range alignment based on ultrasonic sensing is provided. The system comprises i) a hand-held portable ultrasonic device, and ii) a mountable ultrasonic device. The mountable ultrasonic device registers a pointing location of the hand-held portable electronic device, and determines positional information and short range alignment from three or more pointing locations of the hand-held portable electronic device. The mountable ultrasonic device conveys the pointing location to a remote system that can display the pointing location and an orientation of the hand-held portable ultrasonic device.

The hand-held portable ultrasonic device includes three ultrasonic transmitters for each transmitting a first, second and third pulse shaped ultrasonic signal through the air, an electronic circuit for generating driver signals to the three ultrasonic transmitters for generating the first, second and third pulse shaped ultrasonic signal, an user interface that receives user input for registering a pointing location of the wand device responsive to the user input, a communications port for relaying the user input and receiving timing information to control the electronic circuit, and a battery for powering the electronic circuit and associated electronics on the first device.

The mountable ultrasonic device includes a processor for generating timing information that includes pulse shape parameters, and processing received pulse shaped ultrasonic signals, a communications interface for transmitting the timing information to a hand-held portable ultrasonic device that in response shapes and transmits a first, second and third pulse shaped ultrasonic signal according to the timing information, three microphones for each receiving the first, second and third pulse shaped ultrasonic signals transmitted through the air, a memory for storing the first, second and third pulse shaped signals to produce a history of received first, second and third pulse shaped signals, and a battery for powering the processor and associated electronics on the second device.

Figure 1A:
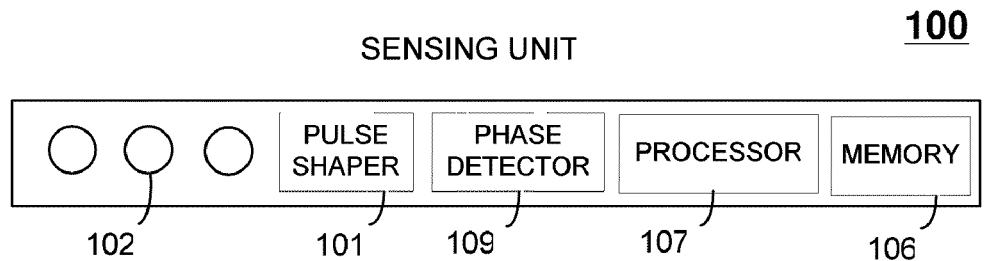
FIG. 1A is a pulse shaping sensing unit for range detection in accordance with one embodiment.

FIG. 1A shows a sensing unit 100 for short range detection. The sensing unit 100 can include a pulse shaper 101 for producing a pulse shaped signal, at least one transmit sensor 102 for transmitting the pulse shaped signal, and at least one receive sensor 102 for receiving the pulse shaped signal. The transmit sensor 102 and receive sensor 102 can be the same element to provide both transmit and receive operations. A processor 107 operatively coupled to the sensors identifies a location and orientation of the sensing unit 100 from the pulse shaped signal received and reflecting off an object, and a memory 106 for storing a history of pulse shaped signals and associated parameters. The receive sensor 102 can be operatively coupled to the pulse shaper 101 and the phase detector 109. The phase detector 109 can identify a phase of the pulse shaped signal, and the processor 107 can use the phase to identify the location and orientation of the sensing unit 100. The processor 107 can include additional processing logic such as thresholds, comparators, logic gates, and clocks for detecting an object's motion.

The sensors 102 can be an array (e.g., line, rows, cols, etc.) or other arranged pattern (e.g., cross, triangle, circle, etc.) of sensing elements. As one example, the sensing element 102 can be an ultrasonic transmitter and ultrasonic receiver for transmitting and receiving ultrasonic signals. In another arrangement, the sensing element 102 can be an array of microphones and speakers for transmitting and receiving ultrasonic and audio signals. As one example, the sensing unit 100 can employ pulse-echo detection of reflected ultrasonic signals for determining its orientation with respect to an object within its proximity. The sensing unit 100 can be an Application Specific Integrated Circuit (ASIC) or Field Programmable Gate Array (FPGA) or other fabricated electronic or analog component. In another arrangement, the sensing element can be CCD camera elements or MEMS camera elements for processing light.

Figure 1B:
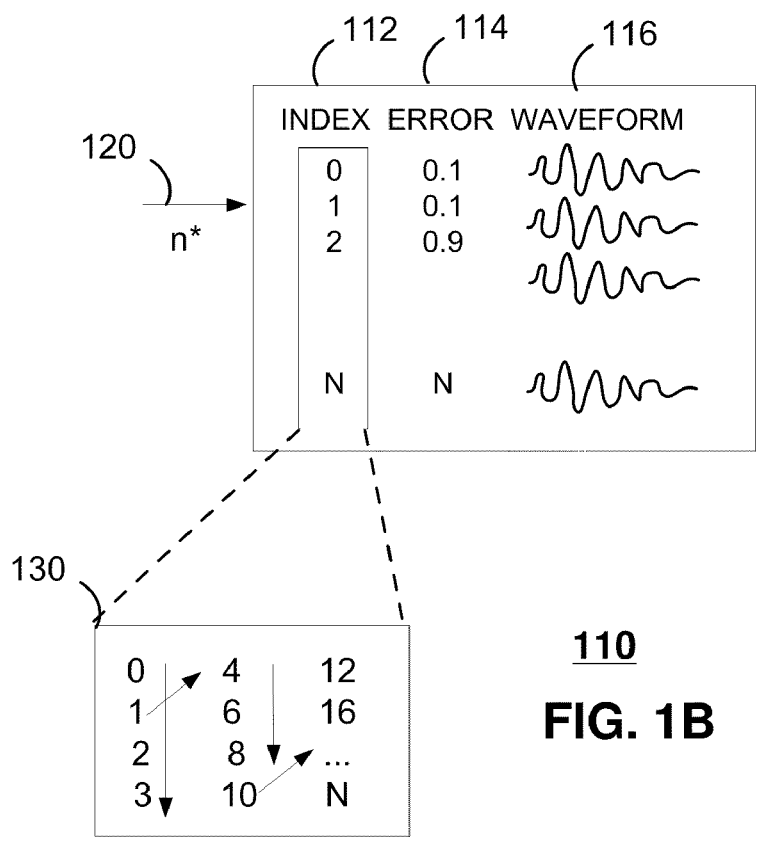
FIG. 1B is an exemplary configuration of a history buffer and indexing table in accordance with one embodiment.

FIG. 1B illustrates an exemplary history 110 stored in the memory 106 for saving transmitted and/or received pulse shaped signals. The history 110 can include an index entry 112, an error entry 114, and a pulse shaped signal waveform entry 116. The error entry can identify errors for nearest pulse shaped signal neighbor as well as all pulse shaped signal waveforms in the history 110 (transmit and receive signals). The error entry 404 can be a matrix.

One method of operation by way of the processor 107 stores the latest N pulse shaped signals (transmit and/or receive) in a memory bank; BANK0. As new pulse shaped signals are received for storage into BANK0, every other (or every $3^{rd}$ $4^{th}$ etc.) pulse shaped signals in BANK0 is moved into another bank; BANK1. Then as pulse shaped signals in BANK1 are replaced, the process of moving every other (or every $3^{rd}$ $4^{th}$, etc.) pulse shaped signals in BANK1 into another bank, call it BANK2, is repeated. This process can continue until sufficient pulse shaped receive signals are stored to realize the $T_{max}$ requirement while significantly reducing the amount of memory required to store the traces.

Figure 2A:
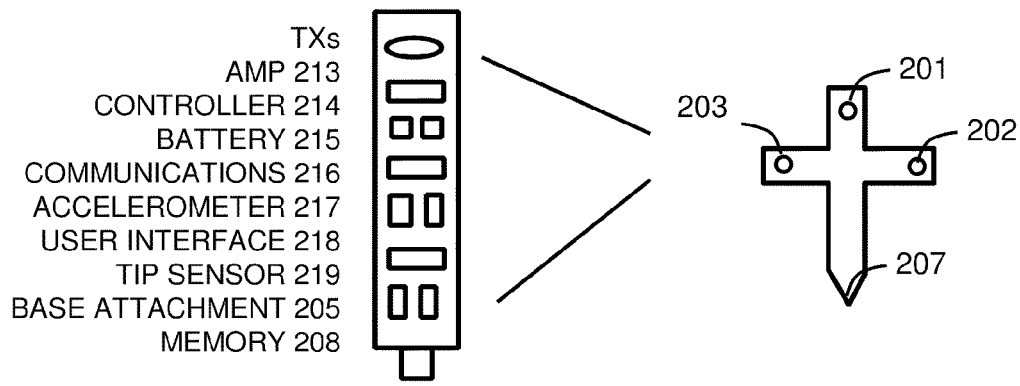
FIG. 2A is a hand-held portable ultrasonic device for registering positional locations in accordance with one embodiment.
Figure 2B:
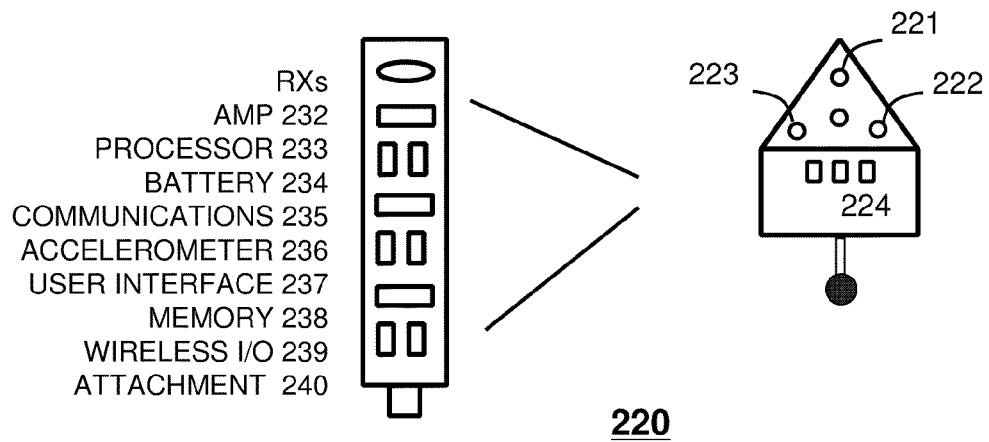
FIG. 2B is a Receiver ultrasonic device for reporting positional locations of the hand-held portable ultrasonic device in FIG. 3 in accordance with one embodiment.

In another arrangement the sensing unit 100 can be partitioned out to a first device and a second device to separate the transmit operation from the receive operation. In this configuration, a system for short range tracking via ultrasonic sensing is provided. FIG. 2A illustrates one embodiment of a first device 200 with TXs (transmit sensors) 201-203 to provide transmit operation. FIG. 2B illustrates one embodiment of a second device 220 with RXs (receive sensors) 221-222 to provide receive operation.

The first device 200 shown in FIG. 2A comprises three ultrasonic transmitters 201-203 for each transmitting a first, second and third pulse shaped signal through the air, an electronic circuit (or controller) 214 for generating driver signals to the three ultrasonic transmitters 201-203 for generating the first, second and third pulse shaped signal, an user interface 218 that receives user input for performing short range alignment determination, a communications port 216 for relaying the user input and receiving timing information to control the electronic circuit 214, and a battery 215 for powering the electronic circuit 215 and associated electronics on the first device 200. The first device 200 102 can include an attachment mechanism 205 for coupling to a structure, bone or jig. The first device 200 may contain more or less than the number of components shown; certain component functionalities may be shared as integrated devices.

Additional ultrasonic sensors can be included to provide an over-determined system for three-dimensional sensing. The ultrasonic sensors can be MEMS microphones, ultrasonic receivers, ultrasonic transmitters or combination thereof. As one example, each ultrasonic transducer can perform separate transmit and receive functions. One example of an ultrasonic sensor is disclosed in U.S. patent application Ser. No. 11/683, 410 entitled "Method and Device for Three-Dimensional Sensing" filed Mar. 7, 2007 the entire contents of which are hereby incorporated by reference. The ultrasonic sensor can transmit pulse shaped waveforms in accordance with physical characteristics of a customized transducer and provided waveform construction shape.

A tip 207 of the first device 200 indirectly identifies points of interest on a structure, for example, a rod, bone, instrument or jig in three-dimensional space. Although the tip is not equipped with ultrasonic transducers, its spatial location in three-dimensional space is established by the three ultrasonic transmitters 201-203. It can be held in the hand as a wand to identify via the (wand) tip 207, points of interest such as (anatomical) features on the structure, bone or jig. The tip 207 can be touch sensitive to registers points responsive to a physical action, for example, touching the tip to an anatomical or structural location. The tip can comprise a mechanical accelerometer or actuated spring assembly. In another arrangement it includes a capacitive touch tip or electrostatic assembly for registering touch.

The user interface 218 can include one or more buttons to permit handheld operation and use (e.g., on/off/reset button) and illumination elements to provide visual feedback. The first device 200 may further include a haptic module with the user interface 218. As an example, the haptic module may change (increase/decrease) vibration to signal improper or proper operation. The first device 200 provides material to cover the transmitters 201-202 to be transparent to sound (e.g., ultrasound) and light (e.g., infrared) yet impervious to biological material such as water, blood or tissue. In one arrangement, a clear plastic membrane (or mesh) is stretched taught; it may vibrate under resonance with a transmitted frequency. The battery 215 can be charged via wireless energy charging (e.g., magnetic induction coils and super capacitors).

The first device 100 can include a base attachment mechanism 205 for coupling to a structure, bone or a jig. As one example, the mechanism can be a magnetic assembly with a fixed insert (e.g., square post head) to permit temporary detachment. As another example, it can be a magnetic ball and joint socket with latched increments. As yet another example, it can be a screw post to an orthopedic screw.

The first device 200 can further include an amplifier 213 and an accelerometer 217. The amplifier enhances the signal to noise ratio of transmitted or received signals. The accelerometer 217 identifies 3 and 6 axis tilt during motion and while stationary. The communications module 216 may include components (e.g., synchronous clocks, radio frequency 'RF' pulses, infrared 'IR' pulses, optical/acoustic pulse) for signaling to the second device 220 (FIG. 2B). The controller 214, can include a counter, a clock, or other analog or digital logic for controlling transmit and receive synchronization and sequencing of the sensor signals, accelerometer information, and other component data or status. The battery 215 powers the respective circuit logic and components.

The controller 214 can utilize computing technologies such as a microprocessor (μP) and/or digital signal processor (DSP) with associated storage memory 108 such a Flash, ROM, RAM, SRAM, DRAM or other like technologies for controlling operations of the aforementioned components of the device. The instructions may also reside, completely or at least partially, within other memory, and/or a processor during execution thereof by another processor or computer system. An Input/Output port permits portable exchange of information or data for example by way of Universal Serial Bus (USB). The electronic circuitry of the controller can comprise one or more Application Specific Integrated Circuit (ASIC) chips or Field Programmable Gate Arrays (FPGAs), for example, specific to a core signal processing algorithm. The controller can be an embedded platform running one or more modules of an operating system (OS). In one arrangement, the storage memory may store one or more sets of instructions (e.g., software) embodying any one or more of the methodologies or functions described herein.

The second device 220 shown in FIG. 2B comprises a processor 233 for generating timing information, registering a pointing location of the first device 200 responsive to the user input, and determining short range alignment from three or more pointing locations of the first device 200 with respect to the second device 220. It includes a communications interface 235 for transmitting the timing information to the first device 200 that in response transmits the first, second and third pulse shaped signals. The pulse shaped signals are a combination of amplitude modulation, frequency modulation, and phase modulation. Three microphones 221-223 each receive the first, second and third pulse shaped signals transmitted through the air. The memory 238 stores the first, second and third pulse shaped signals to produce a history of pulse shaped signals. The wireless communication interface (Input/Output) 239 wirelessly conveys the positional information and the short range alignment of the three or more pointing locations to a remote system. The remote system can be a computer, laptop or mobile device that displays the positional information and alignment information in real-time as described ahead. The battery powers the processor 233 and associated electronics on the second device 220. The second device 200 may contain more or less than the number of components shown; certain component functionalities may be shared or therein integrated.

Additional ultrasonic sensors can be included to provide an over-determined system for three-dimensional sensing. The ultrasonic sensors can be MEMS microphones, ultrasonic receivers, ultrasonic transmitters or combination thereof. As one example, each ultrasonic transducer can perform separate transmit and receive functions. One example of an ultrasonic sensor is disclosed in U.S. patent application Ser. No. 11/683, 410 entitled "Method and Device for Three-Dimensional Sensing" the entire contents of which are hereby incorporated by reference. The second device 220 can include an attachment mechanism 240 for coupling to bone or a jig. As one example, the mechanism 240 can be a magnetic assembly with a fixed insert (e.g., square post head) to permit temporary detachment. As another example, it can be a magnetic ball and joint socket with latched increments.

The second device 220 can further include an amplifier 232, the communications module 235, an accelerometer, and processor 233. The amplifier 232 enhances the signal to noise of transmitted or received signals. The processor 233 can include a controller, counter, a clock, and other analog or digital logic for controlling transmit and receive synchronization and sequencing of the sensor signals, accelerometer information, and other component data or status. The accelerometer 236 identifies axial tilt (e.g., 3/6 axis) during motion and while stationary. The battery 234 powers the respective circuit logic and components.

The communications module 235 can include components (e.g., synchronous clocks, radio frequency 'RF' pulses, infrared 'IR' pulses, optical/acoustic pulse) for local signaling (to wand 102). It can also include network and data components (e.g., Bluetooth, ZigBee, Wi-Fi, GPSK, FSK, USB, RS232, IR, etc.) for wireless communications with a remote device (e.g., laptop, computer, etc.). Although external communication via the network and data components is herein contemplate, it should be noted that the second device 220 can include a user interface 237 to permit standalone operation. As one example, it can include 3 LED lights 224 to show three or more Wand tip pointing location alignment status. The user interface 237 may also include a touch screen or other interface display with its own GUI for reporting positional information and alignment.

The processor 233 can utilize computing technologies such as a microprocessor (μP) and/or digital signal processor (DSP) with associated storage memory 108 such a Flash, ROM, RAM, SRAM, DRAM or other like technologies for controlling operations of the aforementioned components of the terminal device. The instructions may also reside, completely or at least partially, within other memory, and/or a processor during execution thereof by another processor or computer system. An Input/Output port permits portable exchange of information or data for example by way of Universal Serial Bus (USB). The electronic circuitry of the controller can comprise one or more Application Specific Integrated Circuit (ASIC) chips or Field Programmable Gate Arrays (FPGAs), for example, specific to a core signal processing algorithm or control logic. The processor can be an embedded platform running one or more modules of an operating system (OS). In one arrangement, the storage memory 238 may store one or more sets of instructions (e.g., software) embodying any one or more of the methodologies or functions described herein.

Figure 3A:
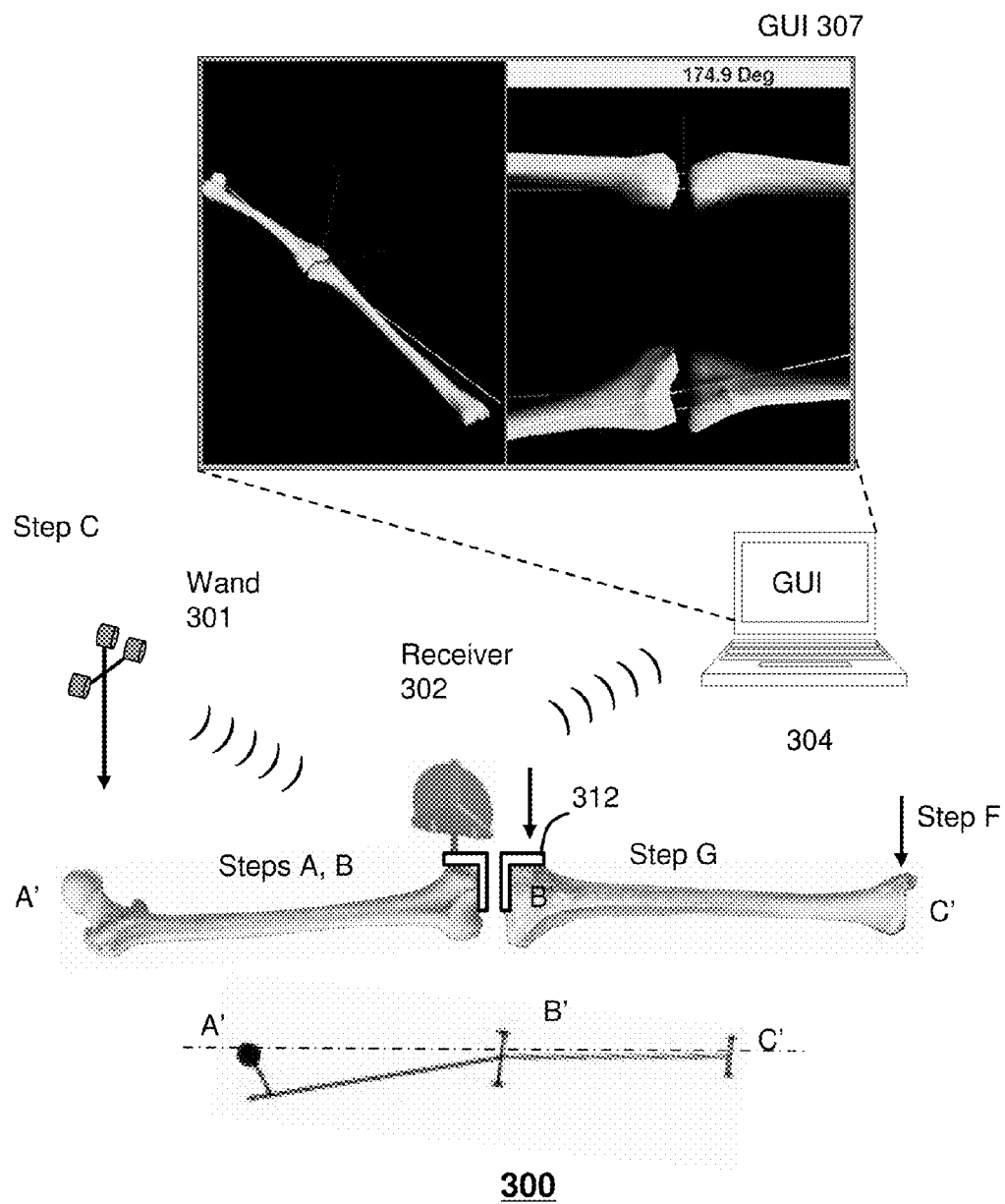
FIG. 3A is an exemplary system for reporting pointing location and alignment in accordance with one embodiment.

FIG. 3A depicts one exemplary embodiment of a system 300 using the first device 200 and second device 220 suitable for use as a positional measurement and alignment tool for orthopedic applications. The example illustrated is a system and method for intra-operatively assesses alignment of the femur and tibia bones.

The system 300 includes the hand-held portable ultrasonic device 301 (hereinafter Wand) and the optional mountable ultrasonic device 302 (hereinafter Receiver). The Wand 301 and Receiver 302 are low cost disposable components that can be delivered in a sterilized package. The Receiver 302 can communicate with the remote system 304 to report wand tip location, positional information and an orientation of the wand 301 in real-time. The Wand 301 and the Receiver 302 communicate directly with one another without outside reliance on a supervisory system; that is, the receiver 302 can determine the location and orientation of the Wand 301 within local view and with respect to its own coordinate system.

The Wand 301 is used to register points of interest in three-dimensional space with respect to the Receiver 302; points of interest can be spatial locations, for example, anatomical or structural locations on a bone or structure 312. The Wand 301 can also measure and report distance (e.g., mm, cm) between registered spatial points, for example, a gap distance between the distal femur and proximal tibia to determine a suitable sized insert. It can also be used to identify displacement, for example, an edge point or perimeter trace of an insert relative to its projected insertion location. The Wand 301 can also thereafter be affixed at these locations to report rotations and translations of the underlying object (e.g., bone, jig, insert, prosthetic etc) at these points, for example, relative to a reference orientation. This also permits for full range tracking and reporting of kinematic behavior. Such information can be used during the surgery to report range of joint motion and for comparison of post-surgical results.

In one embodiment, the system 300 comprises the Receiver 302 coupled to the jig 312, and the Wand 301 to register points of interest on a first and second bone with respect to the jig 312. The Receiver 302 and Wand 301 employ ultrasonic sensing and tracking to determine the Wands orientation and location relative to the Receiver 302 and the jig 312. Based on the registered points of interest, the Receiver 302 assesses and reports parameters related to the orientation of the jig 312 for aligning the first and second bone. The wand tip locations and orientations can also be stored for reference on the Receiver 302. Similarly, the system 300 can report alignment of the bones or jigs 312 by way of the Wand 301 and the Receiver 302 from these points of interest. The system 300 can assist in assessing alignment of the jigs 312 and bones for example, in knee replacement procedures. Software configurable parameters permit operation beyond the 3 m application range shown.

In one example, alignment is achieved when the points of the femur head (A'), knee center (B') and ankle (C') are positioned in a straight line as indicated by a positioning location of the Wand tip 301 at the second locations at separate times. Femur head identification of point (A') can be determined by affixing the Receiver 302 to the distal end of the femur and placing the Wand 301 at a stationary location in view (e.g., 1 m distance from Receiver 302). The femur is then rotated in a pattern for approximately 10-15 seconds to resolve the spherical center (femur head) as described in Provisional Patent Application No. 61/291,725 while the hip is sufficiently still. Upon establishing point (A'), the wand tip is then used to register the knee center (e.g., distal femur center) point B' when the leg is in flexion. Other anatomical locations can be registered fro providing further alignment information, for example, the proximal tibia. Thereafter, the wand tip is used to register the medial malleolus and the lateral malleolus which establishes the ankle center C' (e.g., eq: center=0.6*medial<x,y,z>)+0.4*lateral<x,y,z>).

Once these three (or more) points A', B' and C' are registered, the Wand 301 can be affixed midway on the tibia and in view of the Receiver 302. This permits real-time tracking of the tibia relative to the femur bone when the leg is in extension (straight) or in flexion (bent). In this fixed relationship, the Receive 302 can track a position and orientation of the Wand 301 relative to the Receiver's own coordinate system which inherently reveals any rotations and translations of the tibia relative to the femur (e.g., axial twist, left-right, up-down, forward-backward, and combinations thereof). As noted previously, this permits the system 300 to track and report a range of motion and associated kinematic information (e.g., axial twist, rotations, alignment) in accordance with a patient's expected orthopedic behavior during the procedure.

Certain aspects of alignment preparation can be performed before hand; for example, calibrating the Receiver 302 to the jig 312 or Wand 301. It can also transmit the positional information to associated wireless devices (e.g., laptop, cell phone, net book) like the remote system 304 and upload the information to a server on a network for example one connected to electronic medical or health care records. The system 300 can assess and report in real-time the position of these points for determining alignment, or other registered points, by way of a graphical user interface on the communication device 304.

Figure 3B:
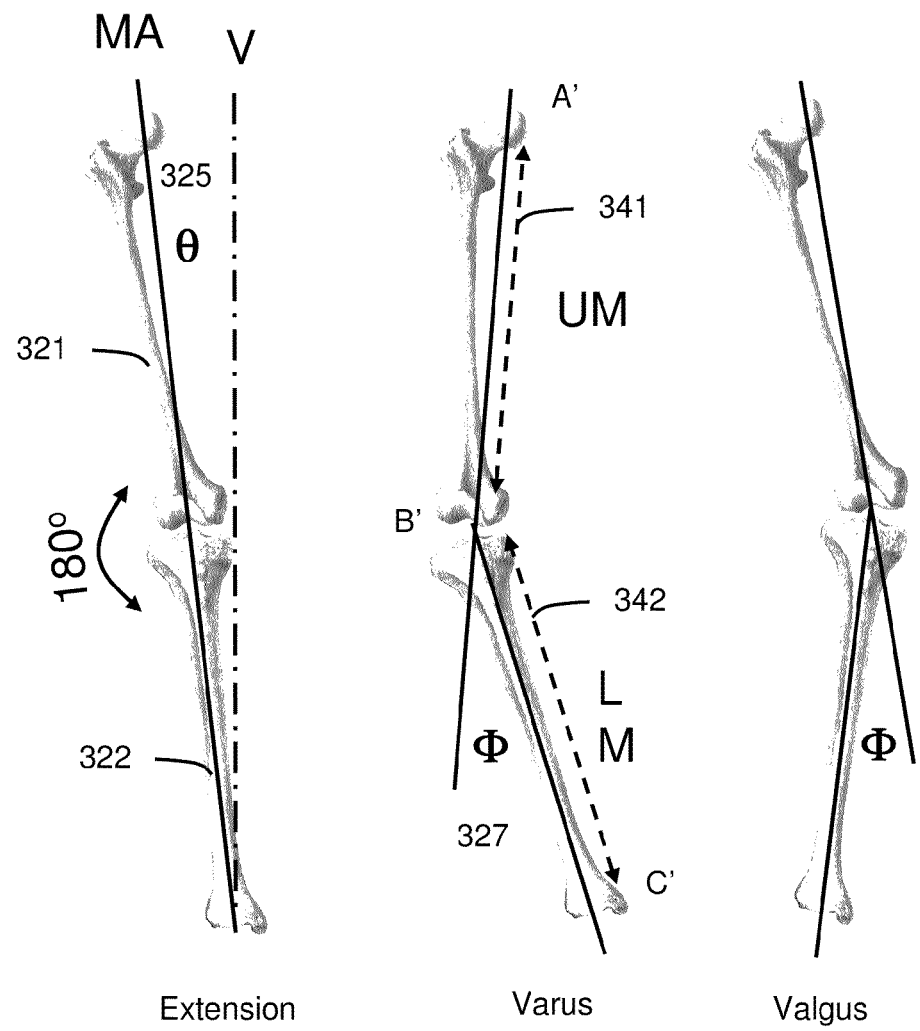
FIG. 3B is an illustration of extension, varus and valgus deviations with respect to mechanical axis alignment.

FIG. 3B shows alignment along a mechanical axis of a leg for normal and abnormal conditions. In extension, the femur 321 and tibia 322 of the leg are aligned along the mechanical axis (MA). The MA is approximately $\theta \sim = 6$ degrees 325 from the vertical (V) at the ankle; and approximately 15-18 degrees from the vertical (V) at the knee (Q-angle) for a straight leg in standing position. As illustrated in the center subplot, a varus deformity is an outward angulation of the distal segment of a bone or joint with an alignment angle (or error) described by $-\Phi 327$. As illustrated in the right subplot a valgus deformity is a term for the inward angulation of the distal segment of a bone or joint with an alignment angle (or error) described by $+\Phi 327$.

The system 300 reports the alignment angle $\Phi 327$ between the first line 341 and the second line 342 as part of the positional location (information). The first line 341 is defined by the pointing location of the Wand 301 at a first point A' at a first time and a second point B' at a second time. The second line 342 is defined by the pointing location of the Wand 301 at the second point B' and a third point C' at a third time. The pointing locations as determined by the pulse shaped signals are stored in the history for reference. The system 300 can include multiple points for determining alignment and is not limited to a 3-point profile.

As previously indicated the Receiver 302 itself can display alignment information or report the information to remote system to provide visualization. As one example, the LED lights 224 on the Receiver 302 illuminate in accordance with a detected alignment. A single multi-color LED will turn green for perfect alignment (0°), turn yellow if less than 2°, and turn red if alignment is off by 3° or more. With single color LEDS, a varus condition will illuminate the corresponding medial (inside) LED, a valgus condition will illuminate the corresponding lateral (outside) LED, and an alignment less than 1° will show all LEDS green. Other illumination patterns are herein contemplated and are not limited to those described. Similarly, the GUI 307 can report alignment information via text representation of the alignment error or by color coding displayed line segments.

Figure 4:
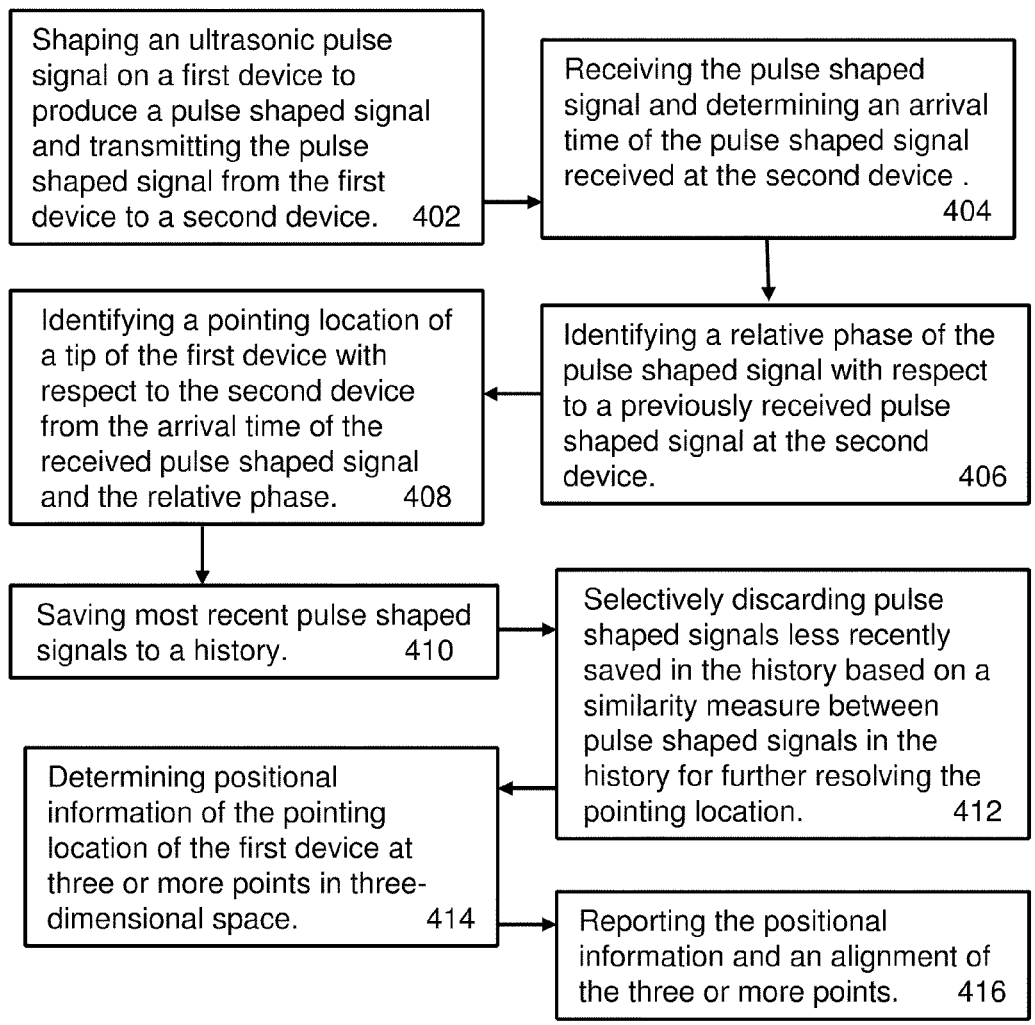
FIG. 4 is a method for short range alignment using ultrasonic sensing in accordance with one embodiment.

FIG. 4 depicts an exemplary method 400 for short range alignment using ultrasonic sensing by way of the alignment system shown in FIG. 3A. The method 400 can be practiced with more or less than the number of steps shown and is not limited to the order shown. To describe the method 400, reference will be made to FIGS. 2A, 2B, 3A and 5, although it is understood that the method 400 can be implemented in any other suitable device or system using other suitable components. Moreover, the method 400 is not limited to the order in which the steps are listed in the method 400 In addition, the method 400 can contain a greater or a fewer number of steps than those shown in FIG. 4

The method can begin at step 402 in which the Wand 301 shapes an ultrasonic pulse signal to produce a pulse shaped signal and at some separation distance transmits the pulse shaped signal to the Receiver 302. The transmitter 201 receives from the controller 214 a driver signal that describes the pulse shape to be transmitted. As one example the shape can be a square wave that causes a transducer of the transmitter 201 to resonate. In another arrangement, the driver signal can be a frequency modulated or amplitude modulated driver signal provided by the controller 214. One example of pulse shaping is taught in U.S. Pat. No. 7,414,705 entitled "Method and System for Range Measurement" the entire contents of which are hereby incorporated by reference.

The pulse shape can be previously stored in a local memory of the controller or external memory 208 that is referenced prior to transmission. Alternatively, timing information provided to the controller 214 from the Receiver 302 can include pulse shape information or pulse shape parameters in real-time; that is, the Receiver 302 directs the Wand 301 to transmit ultrasonic pulse signals with a specified shape and at a specified time. The shaping comprises generating an amplitude modulated region, frequency modulated region, constant frequency region, phase modulated region, a chirp region, or a combination thereof as described ahead in FIG. 5.

The Receiver 302 by way of the processor 233 at step 404 receives the pulse shaped signal and determines an arrival time of the received pulse shaped signal. One example of detecting arrival time is taught in U.S. patent application Ser. No. 11/562,404 entitled "Method and System for Object Control" the entire contents of which are hereby incorporated by reference. This can further include calculating a first Time of Flight of a first pulse shaped signal emitted at a first time from a first transmitter on the first device and received on a first microphone on the second device, calculating a second Time of Flight of a first pulse shaped signal emitted at a second time from a second transmitter on the first device and received on a second microphone on the second device, and calculating a third Time of Flight of a first pulse shaped signal emitted at a third time from a third transmitter on the first device and received on a third microphone on the second device. That is, a time of flight is calculated for each microphone based on the transmitting of only one pulse shaped waveform.

In a first arrangement, the Receiver 302 is wired via a tethered electrical connection (e.g., wire) to the Wand 301. That is, the communications port of the Wand 301 is physically wired to the communications interface of the Receiver 302 for receiving timing information. The timing information from the Receiver 302 tells the Wand 301 when to transmit and includes optional parameters that can be applied to the ultrasonic signal for pulse shaping. The processor on the Receiver 302 employs this timing information to establish the first, second and third Time of Flight measurements with respect to a reference time base.

In a second arrangement, the Receiver 302 is communicatively coupled to the Wand 301 via a wireless signaling connection. As previously indicated an infrared transmitter on the Wand 301 can transmit an infrared timing signal with each transmitted pulse shaped signal. The Receiver 302 can include a photo diode for determining when the infrared timing signal is received. In this case the communications port of Wand 301 is wirelessly coupled to the communications interface of the Receiver 302 by way of the infrared transmitter and the photo diode for relaying the timing information to within 3 microsecond accuracy (~1 mm resolution). The processor on the Receiver 302 employs this infrared timing information to establish the first, second and third Time of Flight measurements with respect to a reference transmit time.

At step 406, the Receiver 302 by way of the processor 233 identifies a relative phase of the pulse shaped signal with respect to a previously received pulse shaped signal. One example of detecting relative phase is taught in U.S. patent application Ser. No. 11/146,445 the entire contents of which are hereby incorporated by reference. This can further include calculating a first phase differential between the first pulse shaped signal and a previously received pulse shaped signal both captured at the first microphone, calculating a second phase differential between the first pulse shaped signal and a previously received pulse shaped signal both captured at the second microphone; and calculating a third phase differential between the first pulse shaped signal and a previously received pulse shaped signal both captured at the third microphone. That is a differential time of flight is calculated for each microphone based on the transmitting of a first pulse shaped waveform and a previously received pulse shaped waveform each at the respective microphone stored in the history.

The Receiver 302 by way of the processor 233 at step 408, identifies a pointing location of the Wand 301 tip 207 with respect to a coordinate system of the Receive 302 from the arrival time of the received pulse shaped signal and the relative phase. The processor 233 converts the time of flight and differential time of flight measurements calculated from each of the received pulse shaped signals at the three microphones to three spatial points, and transforms the three spatial points to X, Y and Z rotations at the positional location to determine an orientation of the first device. A positional location is where the wand tip 207 is located in three-dimensional space with respect to an orientation of the Wand 301. The positional location can be represented in Cartesian <x,y,z> coordinates or r*sin/cos polar coordinates. It can be the same point in three-dimensional space even though the wand orientation (e.g., tilt, rotation).

Continuing with method 400, as shown in step 410, most recent pulse shaped signals are saved to a history, and at step 412 pulse shaped signals less recently saved in the history are selectively discarded. The selective pruning of pulse shaped signals in the history is based on a similarity measure between previous pulse shaped signals for further and more efficiently resolving the pointing location. This approach saves most recent n (index 403 into history) or n small, since there are typically many echo waveform changes in the near time. In contrast, the echoes from far-time (past time) can be selectively pruned based on current distance measures (e.g., L2 norm, spectral distortion, log-likelihood, MSE, energy metrics). In practice, the most recent n echoes can be saved, and echoes from longer ago in the history can be selectively discarded based on the distances, to create a sparse history that is weighted more heavily in the near-time than in the far-time.

The step of selectively discarding pulse shaped signals includes selectively pruning the history based on one among an L2 norm based, spectral distortion based, log-likelihood based, or mean-squared error based metric, creating a sparse history of pulse shaped signals based on a difference rate between pulse shaped signals, and updating an index table to the pulse shaped signals in the history according to the sparse history, wherein the sparse history weights echoes more heavily in the near-time than in the far-time. This step can further include iteratively scanning through the history to identify an index 112 for the pulse shaped signals where an distortion difference (e.g. error 114) is significantly greater than a noise difference.

At step 414, the Receiver 302 determines positional information of the pointing location of the Wand 301 at three or more points in three-dimensional space. The Wand 301 and the Receiver 302 each have their own local coordinate system. The Receiver 302 maps the wand coordinate system to its own local coordinate system by a series of translations and rotations given the transmitter locations on the Wand 301 and the microphone locations on the Receiver 302. One example of mapping coordinates via ultrasonic sensing is taught in U.S. patent application Ser. No. 11/566,148 entitled "Method and System for Mapping Virtual Coordinates" the entire contents of which are hereby incorporated by reference.

The Receiver 302 determines time of flight and relative phase of the received pulse shaped signals at each of the microphones, and calculates the spatial locations of the Wand 301 transmitters with respect to the Receivers 302 local coordinate system (at the origin). The Receiver 302 thereafter applies a series of translations and rotations to map the Wand's 301 local coordinate system to the Receiver's 302 local coordinate system. This transformation establishes an orientation of the Wand 301 and positional location of the wand tip relative to the Receiver 302. The mapping includes i) the Wand 301 dimensions (e.g., 10×3×10 cm <w,l,h>) and component layout for the local coordinates of the transmitters and the wand tip that are predetermined, and ii) the Receiver 302 dimensions (e.g., 6×2×8 cm, <w,l,h>) and component layout for the local coordinates of the microphones and its coordinate origin that are predetermined.

The Receive 302 at step 416 reports the positional information and an alignment of the three or more points. The positional information identifies the Wand 301 tip location relative to the Receiver 302 and optionally the spatial coordinates of the three or more Wand 301 transmitters relative to the coordinate system of the Receiver 302. It can be reported via sensory feedback, graphical or text display and/or audibly. One example of sensory feedback via ultrasonic sensing and its principles of operation is taught in U.S. patent application Ser. No. 11/562,413 entitled "Method and System for Sensory Feedback" the entire contents of which are hereby incorporated by reference. As shown in FIG. 3A, the positional information and the alignment can be rendered to a 3D representation; for example, alignment of the femur and tibia. The GUI 307 displays real-time updates to permit the user to visualize and assess multiple-point alignment. In the example shown, alignment is reported for varus and valgus deviations in accordance with the wand tip positional locations.

The method 400 repeat operation of the method steps 402 to 416 to continually update the positional location of the Wand 301 tip and the Wand's orientation. That is, the Receiver 302 continually tracks the Wand 301 location as it is moved in three-dimensional space. It can update the GUI 307 in response to a user directive when the user presses the wand button to register a point. The Wand 301 can also be independently mounted to another object to report position and orientation of that object. This permits the system 300 to track relative movement or position of one object (e.g., femur) with respect to another object (e.g., tibia).

In another embodiment, a method for short range alignment using ultrasonic sensing is provided. The method includes shaping three ultrasonic pulse signals on a first device to generate three pulse shaped signals and transmitting the three pulse shaped signals by way of three transmitters on the first device to a second device, receiving the three pulse shaped signals at each of three microphones on the second device and determining three arrival times for the three pulse shaped signals received at the three microphones, identifying three relative phases of the three pulse shaped signals with respect to previously received pulse shaped signals at the three corresponding microphones on the second device, identifying a pointing location of a tip of the first device with respect to a coordinate system of the second device from the three arrival times of the received pulse shaped signals and the three relative phases of the received pulse shaped signals, determining alignment of three or more registered pointing locations of the first device at three or more three-dimensional locations and at separate times by repeated operation of the method steps above, and reporting an alignment of the three or more pointing locations.

Transmit times for each of the three pulse shaped signals can be delayed by transmitting a first ultrasonic pulse signal at a first time, transmitting a second ultrasonic pulse signal at a second time, and transmitting a third ultrasonic pulse signal at a third time. A portion of each pulse shaped signal can include a frequency modulated region, constant frequency region, phase modulated region, or a chirp region. This permits estimating the pointing location from a frequency modulated region for each of the three received pulse shaped signal, and an orientation from the relative phase from a continuous frequency region for each of the three received pulse shaped signals.

The method steps can be repeated to further include saving most recent pulse shaped signals to a history, and selectively discarding pulse shaped signals less recently saved in the history based on a similarity measure between pulse shaped signals in the history for further resolving the pointing location. In a wireless arrangement timing information is transmitted from the first device to the second device to indicate a pulse shape and when to transmit each pulse shaped signal.

Figure 5:
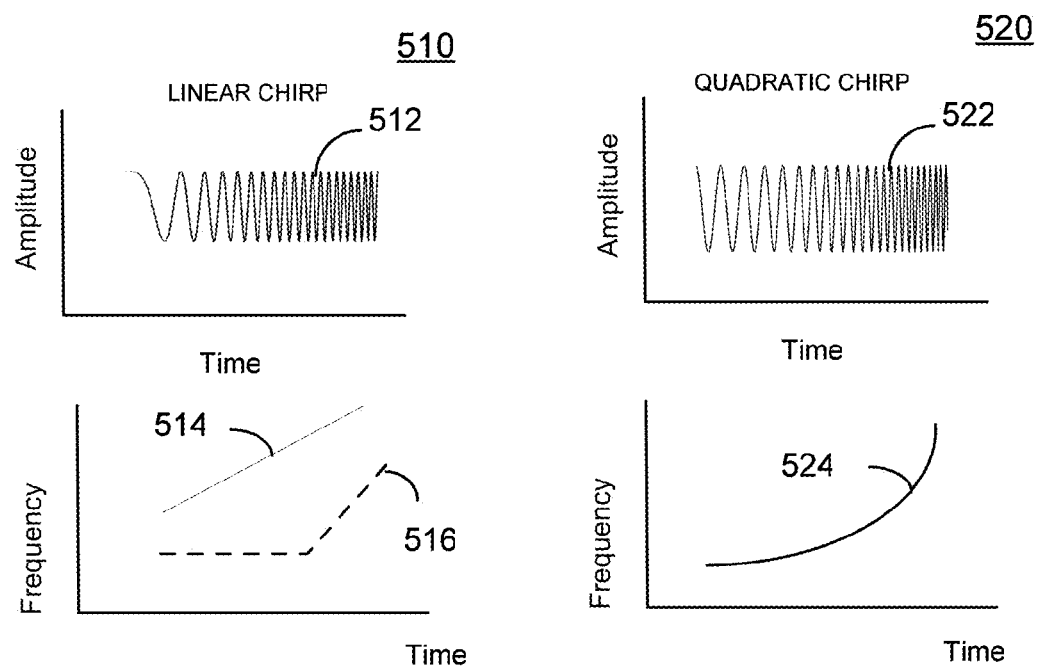
FIG. 5 is an illustration of chirp signals used for short-range detection in accordance with one embodiment.

Referring to FIG. 5, a pair of chirp signals 510 and 520 is shown. Briefly, the chirp signals are sent from the Wand 301 in a direction of the Receiver 302 and captured at the Receiver 302. It should also be noted that in certain embodiments both devices can transmit and receive chirp signals. The chirp signals are condition pulse signals that improve a detection of the pulse.

The pulse shaper can be implemented as a combination of software and hardware on the controller 214 in the Wand 301 (see first device 200). It can produce a linear chirp 510 or a quadratic chirp 520. The pulse shaper by way of the controller 214 can produce numerous types of chirp signals, of which 512 and 522 are provided for illustration. It should also be noted that the second device 220 (Receive 302) can generate pulse shape information that is instead transmitted to the Wand 301 which in response generates the pulse shaped signals. In this case, the Wand 301 receives directives from the Receiver 302 to adjust the shaping and/or timing sequence of transmitted pulse shaped signals.

In one example, the linear chirp 512 can be represented as a frequency modulated sine wave with linearly increasing frequency 514. As another example, the linear chirp 512 can also be represented as a piece-wise linear function shown in 516. For instance, the first portion of the chirp signal 516 can contain constant frequency modulation followed by a second portion which can be a linearly increasing frequency modulation. The chirp signal is not limited to being linearly modulated. For example, the pulse shaper 101 can produce a quadratic chirp signal 520. The quadratic chirp signal 520 can be characterized by a non-linearly varying frequency modulation with a quadratic phase. The chirp signal 522 can be represented by the frequency and time characteristics of plot 524. As can be seen, the frequency increases in an exponential fashion with time. The exponential frequency increase can be seen in the increased periodicity of the time signal 522.

From the foregoing descriptions, it would be evident to an artisan with ordinary skill in the art that the aforementioned embodiments can be modified, reduced, or enhanced without departing from the scope and spirit of the claims described below. For example, the system 300 can be deployed in industrial settings for assessing alignment, medical field for assessing a positional relationship among objects, or mechanical devices or drills for aligned guidance. From the embodiments of FIGS. 1-6 it should be evident to one of ordinary skill in the art that there are innumerable ways to use the sensor system. Accordingly, the reader is directed to the claims for a fuller understanding of the breadth and scope of the present disclosure.

Figure 6:
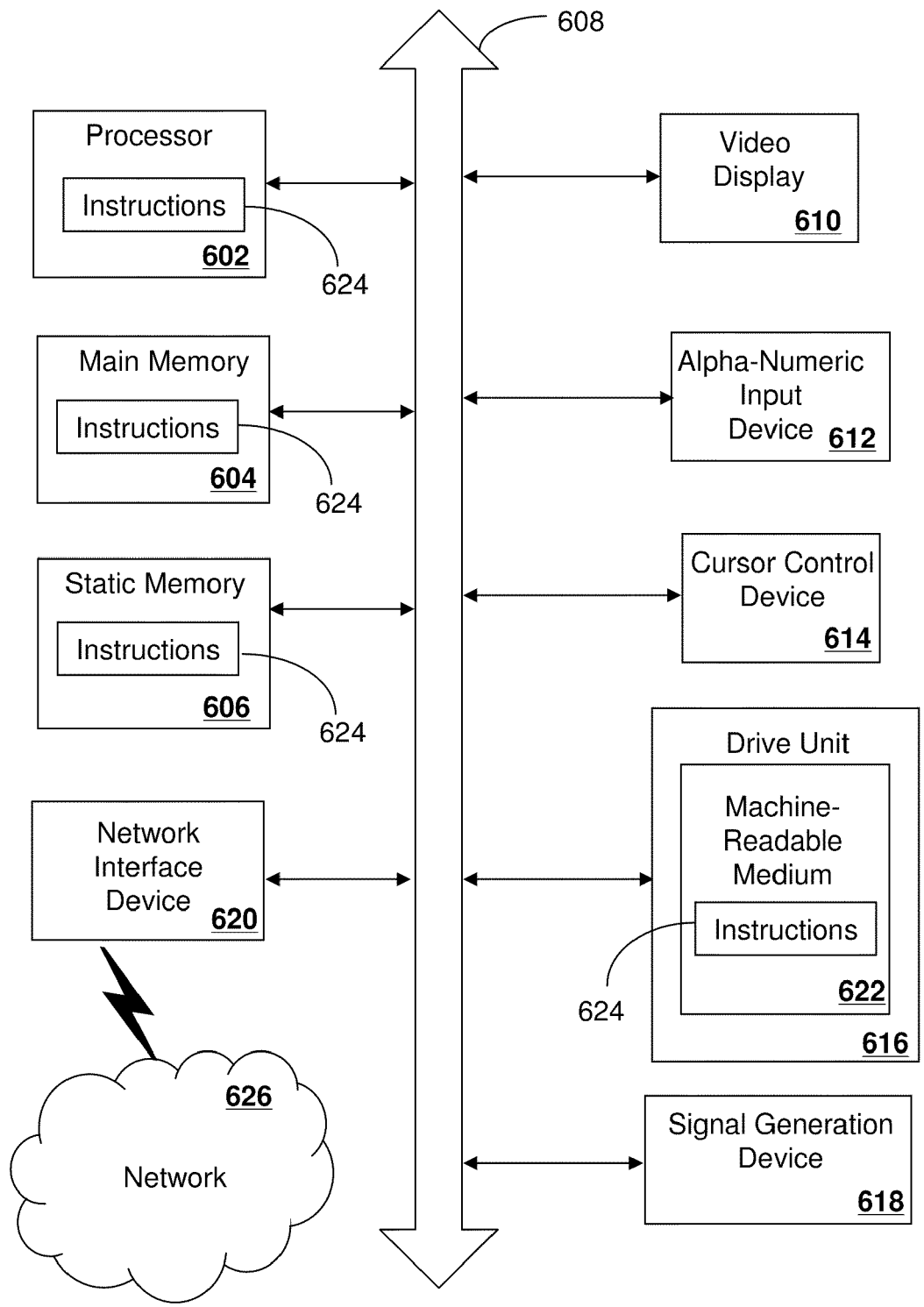
FIG. 6 depicts an exemplary diagrammatic representation of a machine in the form of a computer system within which a set of instructions, when executed, may cause the machine to perform any one or more of the methodologies disclosed herein.

FIG. 6 depicts an exemplary diagrammatic representation of a machine for supporting operation of the sensor device in the form of a computer system 600 within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

The computer system 600 may include a processor 602 (e.g., a central processing unit (CPU), a graphics processing unit (GPU, or both), a main memory 604 and a static memory 606, which communicate with each other via a bus 608. The computer system 600 may further include a video display unit 610 (e.g., a liquid crystal display (LCD), a flat panel, a solid state display, or a cathode ray tube (CRT)). The computer system 600 may include an input device 612 (e.g., a keyboard), a cursor control device 614 (e.g., a mouse), a mass storage medium 616, a signal generation device 618 (e.g., a speaker or remote control) and a network interface device 620.

The mass storage medium 616 may include a computer-readable storage medium 622 on which is stored one or more sets of instructions (e.g., software 624) embodying any one or more of the methodologies or functions described herein, including those methods illustrated above. The computer-readable storage medium 622 can be an electromechanical medium such as a common disk drive, or a mass storage medium with no moving parts such as Flash or like non-volatile memories. The instructions 624 may also reside, completely or at least partially, within the main memory 604, the static memory 606, and/or within the processor 602 during execution thereof by the computer system 600. The main memory 604 and the processor 602 also may constitute computer-readable storage media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 624, or that which receives and executes instructions 624 from a propagated signal so that a device connected to a network environment 626 can send or receive voice, video or data, and to communicate over the network 626 using the instructions 624. The instructions 624 may further be transmitted or received over a network 626 via the network interface device 620.

While the computer-readable storage medium 622 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure.

The term "computer-readable storage medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a computer-readable storage medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP, USB) represent examples of the state of the art. Such standards are periodically superseded by faster or more efficient equivalents having essentially the same functions. Accordingly, replacement standards and protocols having the same functions are considered equivalents.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Other examples of positional measurement and alignment for orthopedic applications are herein contemplated. As another example a system and method for positioning and inserting a hip cup is provided. The Wand tip can register three locations on the hip to identify a docking target for a hip cup. The Wand 301 can then be affixed to a cup insert instrument to track its orientation relative to the registered docking target. A third example is a system and method for visualizing and reporting vertebral alignment in spine applications. The wand tip can register multiple location on the sacrum to identify a base coordinate system. The wand can then be affixed (or touched) to a vertebra to report alignment relative to the sacrum. The Wand can also be used to trace and report a spine contour for before and after comparison.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A method for short range alignment using ultrasonic sensing, comprising:
    shaping an ultrasonic pulse signal on a first device to produce a pulse shaped signal and transmitting the pulse shaped signal from the first device to a second device;
    receiving the pulse shaped signal and determining an arrival time of the pulse shaped signal received at the second device;
    identifying a relative phase of the pulse shaped signal with respect to a previously received pulse shaped signal at the second device;
    identifying a pointing location of a tip of the first device with respect to the second device from the arrival time of the received pulse shaped signal and the relative phase;
    saving most recent pulse shaped signals to a history;
    selectively discarding pulse shaped signals less recently saved in the history based on a similarity measure between pulse shaped signals in the history for further resolving the pointing location;
    determining positional information of the pointing location of the first device at three or more points in three-dimensional space; and
    reporting the positional information and an alignment of the three or more points,
    wherein the shaping uses a combination of amplitude modulation, frequency modulation, and phase modulation.

2. The method of claim 1, comprising estimating the pointing location from a frequency modulated region for the received pulse shaped signal, and an orientation from the relative phase from a continuous frequency region for the received pulse shaped signal.

3. The method of claim 1, comprising
    calculating a first Time of Flight of a first pulse shaped signal emitted at a first time from a first transmitter on the first device and received on a first microphone on the second device;
    calculating a second Time of Flight of a first pulse shaped signal emitted at a second time from a second transmitter on the first device and received on a second microphone on the second device; and
    calculating a third Time of Flight of a first pulse shaped signal emitted at a third time from a third transmitter on the first device and received on a third microphone on the second device.

4. The method of claim 2, comprising
    calculating a first phase differential between the first pulse shaped signal and a previously received pulse shaped signal both captured at the first microphone;
    calculating a second phase differential between the first pulse shaped signal and a previously received pulse shaped signal both captured at the second microphone; and
    calculating a third phase differential between the first pulse shaped signal and a previously received pulse shaped signal both captured at the third microphone; and
    determining the pointing location of the first device from first, second, and third Time of Flight and the first, second and third phase differential.

5. The method of claim 1, further comprising
    converting the time of flight and differential time of flight measurements calculated from each of the received pulse shaped signals at the three microphones to three spatial points;
    transforming the three spatial points to X, Y and Z rotations around the first device at the positional location to determine an orientation of the first device.

6. The method of claim 1, where reporting the alignment identifies an angle between a first line and a second line, where the first line is defined by a first point at a first time and a second point at a second time, and the second line is defined by the pointing location of the first device at the second point and a third point at a third time.

7. The method of claim 1, wherein short range detection between the first device and the second device is 5 cm to 2 m with an angle of the first device and the second device at 60 degrees or less.

8. The method of claim 1, wherein the step of selectively discarding pulse shaped signals comprises:
    selectively pruning the history based on one among an L2 norm based, spectral distortion based, log-likelihood based, or mean-squared error based metric;
    creating a sparse history of pulse shaped signals based on a difference rate between pulse shaped signals; and
    updating an index table to the pulse shaped signals in the history according to the sparse history,
    wherein the sparse history weights echoes more heavily in the near-time than in the far-time.

9. A method for short range alignment using ultrasonic sensing, the method steps comprising:
    shaping three ultrasonic pulse signals on a first device to generate three pulse shaped signals and transmitting the three pulse shaped signals by way of three transmitters on the first device to a second device;
    receiving the three pulse shaped signals at each of three microphones on the second device and determining three arrival times for the three pulse shaped signals received at the three microphones;
    identifying three relative phases of the three pulse shaped signals with respect to previously received pulse shaped signals at the three corresponding microphones on the second device;
    identifying a pointing location of a tip of the first device with respect to a coordinate system of the second device from the three arrival times of the received pulse shaped signals and the three relative phases of the received pulse shaped signals;

determining alignment of three or more registered pointing locations of the first device at three or more three-dimensional locations and at separate times by repeated operation of the method steps above; and reporting an alignment of the three or more pointing locations, wherein at least one portion of each pulse shaped signal is at least one among a frequency modulated region, constant frequency region, phase modulated region, and a chirp region.

10. The method of claim 9, wherein the step of identifying the pointing location comprises:

estimating the pointing location from a frequency modulated region for each of the three received pulse shaped signal, and an orientation from the relative phase from a continuous frequency region for each of the three received pulse shaped signals.

11. The method of claim 9, comprising delaying a transmit time for each of the three pulse shaped signals by:

transmitting a first ultrasonic pulse signal at a first time;

transmitting a second ultrasonic pulse signal at a second time; and transmitting a third ultrasonic pulse signal at a third time.

12. The method of claim 11, comprising:

wirelessly transmitting timing information from the first device to the second device to indicate a pulse shape and when to transmit each pulse shaped signal.

13. The method of claim 9, comprising repeating the method steps to include:

saving most recent pulse shaped signals to a history; and selectively discarding pulse shaped signals less recently saved in the history based on a similarity measure between pulse shaped signals in the history for further resolving the pointing location.

* * * * *